(12) United States Patent
Zhang et al.

(10) Patent No.: US 12,280,185 B2
(45) Date of Patent: Apr. 22, 2025

(54) PLASMA GENERATION DEVICE

(71) Applicant: QIANGGU BIOTECH (SHANGHAI) CO., LTD., Shanghai (CN)

(72) Inventors: Shijun Zhang, Shanghai (CN); Xiaohui Yu, Shanghai (CN)

(73) Assignee: QIANGGU BIOTECH (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 18/706,000

(22) PCT Filed: May 16, 2022

(86) PCT No.: PCT/CN2022/093178
§ 371 (c)(1),
(2) Date: Apr. 30, 2024

(87) PCT Pub. No.: WO2023/077771
PCT Pub. Date: May 11, 2023

(65) Prior Publication Data
US 2024/0424162 A1 Dec. 26, 2024

(30) Foreign Application Priority Data
Nov. 4, 2021 (CN) .......................... 202111303142.1

(51) Int. Cl.
*A61L 9/22* (2006.01)
(52) U.S. Cl.
CPC ...................... *A61L 9/22* (2013.01)
(58) Field of Classification Search
CPC ......................................................... A61L 9/22
See application file for complete search history.

(56) References Cited

U.S. PATENT DOCUMENTS

| 2009/0274592 | A1 | 11/2009 | Bergeron |
| 2020/0251324 | A1 | 8/2020 | Park et al. |
| 2021/0356148 | A1* | 11/2021 | Tulkki ...................... B03C 3/08 |

FOREIGN PATENT DOCUMENTS

| CN | 103731968 A | 4/2014 |
| CN | 105451425 A | 3/2016 |
| CN | 106793442 A | 5/2017 |
| CN | 108339666 A | 7/2018 |
| CN | 110180012 A | 8/2019 |
| CN | 210905502 U | 7/2020 |
| CN | 111589585 A | 8/2020 |

(Continued)

*Primary Examiner* — Kevin Joyner
(74) *Attorney, Agent, or Firm* — Bayramoglu Law Offices LLC (57) ABSTRACT

A plasma generation device relates to the field of environmental disinfection. The plasma generation device includes a frame, a discharge needle, and plasma generating barrels. The plasma generating barrels form an array in the frame, without an inter-barrel gap. The discharge needle is provided on a geometric centerline in each of the plasma generating barrels. A distance from a discharge endpoint of the discharge needle to any point on an edge of the plasma generating barrel is identical. In combination with advantages of a circular cylindrical plasma generating barrel and a square cylindrical plasma generating barrel, the plasma generation device maximizes the ventilation rate and the disinfection efficiency of plasma ionization at a most economical voltage.

13 Claims, 13 Drawing Sheets

(56) References Cited

FOREIGN PATENT DOCUMENTS

| | | | | |
|---|---|---|---|---|
| CN | 113925992 | A | 1/2022 | |
| CN | 216795345 | U | 6/2022 | |
| EP | 0829089 | A1 | 3/1998 | |
| EP | 2460160 | A1 | 6/2012 | |
| GB | 2512303 | A * | 10/2014 | ............... A61L 9/04 |
| WO | 2012125435 | A2 | 9/2012 | |
| WO | 2020224567 | A1 | 11/2020 | |
| WO | 2021182882 | A1 | 9/2021 | |

* cited by examiner

PLASMA GENERATION DEVICE

CROSS REFERENCE TO THE RELATED APPLICATIONS

This application is the national phase entry of International Application No. PCT/CN2022/093178, filed on May 16, 2022, which is based upon and claims priority to Chinese Patent Application No. 202111303142.1, filed on Nov. 4, 2021, the entire contents of which are incorporated herein by reference.

TECHNICAL FIELD

The present disclosure relates to the field of environmental disinfection, and in particular to a plasma generation device.

BACKGROUND

A large number of bacteria, viruses, microorganisms and so on in air can pose a hazard to human health. To ensure cleanliness of air within a certain range, the air can be disinfected. Compared with activated carbon and other filtering methods, plasma disinfection has a stronger effect and a faster acting time.

Figure 1:
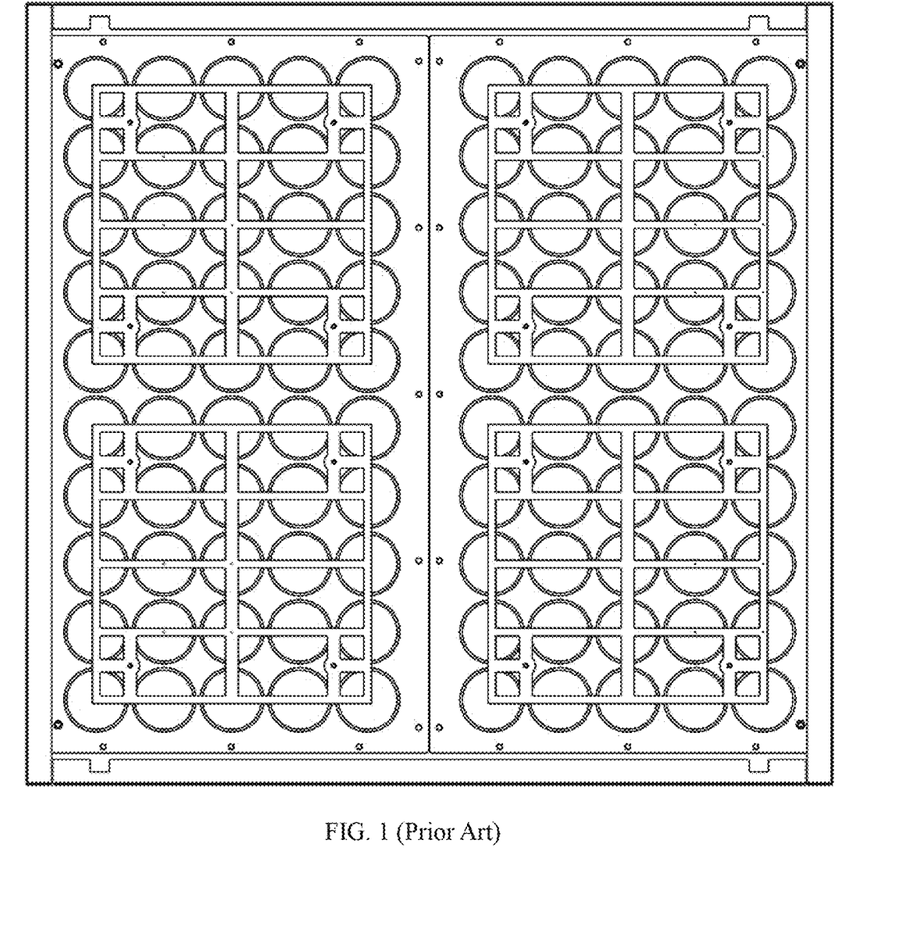
FIG. 1 is a schematic view of a circular cylindrical plasma generating barrel according to a prior art.

An existing plasma air purifier includes a plurality of components, such as an air suction device, a disinfection device, and an air discharge device. The plasma disinfection device includes a plasma generating barrel and a discharge module in the plasma generating barrel. A discharge needle (which is relatively thin, and is fixed on a printed circuit board (PCB)) in the discharge module discharges in the generating barrel to generate a plasma, and air is disinfected by a bottom blower when passing through the generating barrel. According to the prior art, the generating barrels are circular cylinders mostly, as shown in FIG. 1. However, when the circular generating barrels are arranged in a frame of a rectangular shape (or other shapes), inter-barrel gaps are present, which makes a space utilization rate, disinfection efficiency, and ventilation rate not be maximized.

Therefore, efforts are made by those skilled in the art to develop a plasma generation device. Without changing a plasma generation efficiency, this plasma generation device further improves the ventilation rate and the disinfection efficiency.

SUMMARY

In view of defects of the prior art, a technical problem to be solved by the present disclosure is to further improve a ventilation rate and a disinfection efficiency, without changing a plasma generation efficiency.

To achieve the above objective, the present disclosure provides a plasma generation device, including a frame, a first discharge needle, and plasma generating barrels, where the plasma generating barrels form an array in the frame; the first discharge needle is provided on a geometric centerline in each of the plasma generating barrels; and a distance from a discharge endpoint of the first discharge needle to any point on an edge of the plasma generating barrel is identical.

Further, a virtual sphere is formed with the discharge endpoint of the first discharge needle as a center; the sphere is tangent to the edge of the plasma generating barrel; and a resulting tangent line is taken as a new edge of the plasma generating barrel.

Further, the plasma generating barrels do not form an inter-barrel gap.

Further, the plasma generating barrels are square, orthohexagonal, and regular triangular.

Further, the plasma generating barrels are circular.

Further, a second discharge needle is provided at a geometric centerpoint in a gap of the array; a virtual sphere is formed with a discharge endpoint of the second discharge needle as a center; the sphere is tangent to an edge of each of four adjacent plasma generating barrels; and a resulting tangent line is taken as a new edge of the plasma generating barrel.

Further, the discharge endpoint of the first discharge needle is not higher than a lowest point of the new edge of the plasma generating barrel; and the discharge endpoint of the second discharge needle is flush with a highest point of the new edge of the plasma generating barrel.

Further, the plasma generation device further includes a PCB; and the first discharge needle and the second discharge needle are provided on different PCBs.

Further, the plasma generation device further includes the PCB; the first discharge needle is electrically connected to the PCB; and both the first discharge needle and the PCB are provided in a streamwise direction.

Further, the plasma generation device further includes a PCB; two sides of the PCB are provided with the plasma generating barrels; and corresponding plasma generating barrels at the two sides share one discharge needle.

Further, the discharge needle has a high level, and the plasma generating barrel has a low level.

According to the technical solutions provided by the present disclosure, in combination with advantages of a circular cylindrical plasma generating barrel and a square cylindrical plasma generating barrel, the present disclosure maximizes the ventilation rate and the disinfection efficiency of plasma ionization at a most economical voltage.

In order to make the objectives, features and effects of the present disclosure fully understood, the concepts, specific structures and technical effects of the present disclosure are clearly and completely described below in conjunction with the examples and drawings.

DETAILED DESCRIPTION OF THE EMBODIMENTS

Multiple preferred embodiment of the present disclosure will be introduced below with reference to the accompanying drawings, such that the technical contents can be understood clearly and easily. The present disclosure can be embodied by embodiments of many different forms, and the protection scope of the present disclosure is not limited to the embodiments mentioned herein.

In the drawings, components with the same structure are denoted by the same numeral, and components with similar structures or functions are denoted by similar numerals. The size and thickness of each component are randomly shown in the drawings, and the present disclosure does not limit the size and thickness of each component. In order to make the illustration clearer, a thickness of a component is appropriately exaggerated in some places of the drawings.

Embodiment 1

According to the plasma generation device in the embodiment, a circular plasma generating barrel is changed into a square plasma generating barrel. Compared with the conventional circular generating barrel, the inter-barrel gap is eliminated, all effective areas in a frame of the plasma generation device can fall within a plasma generating range, and the effective ventilation rate is maximized with the elimination of the inter-barrel gap. Likewise, in case of a same air volume, a size and a power of a blower can be reduced correspondingly.

Figure 2:
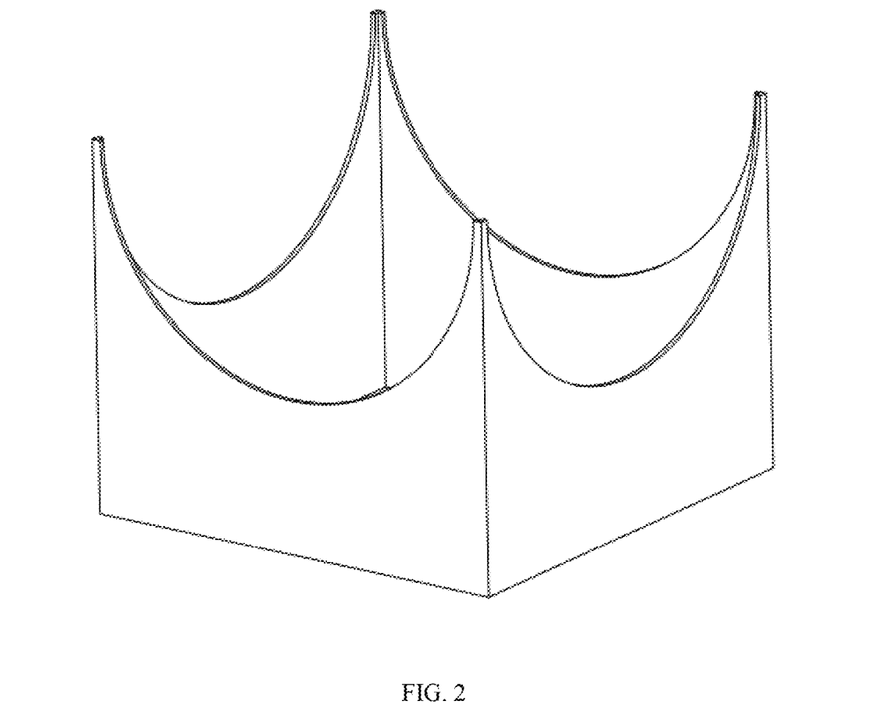
FIG. 2 is a schematic view of a single square plasma generating barrel according to a preferred embodiment of the present disclosure.
Figure 3:
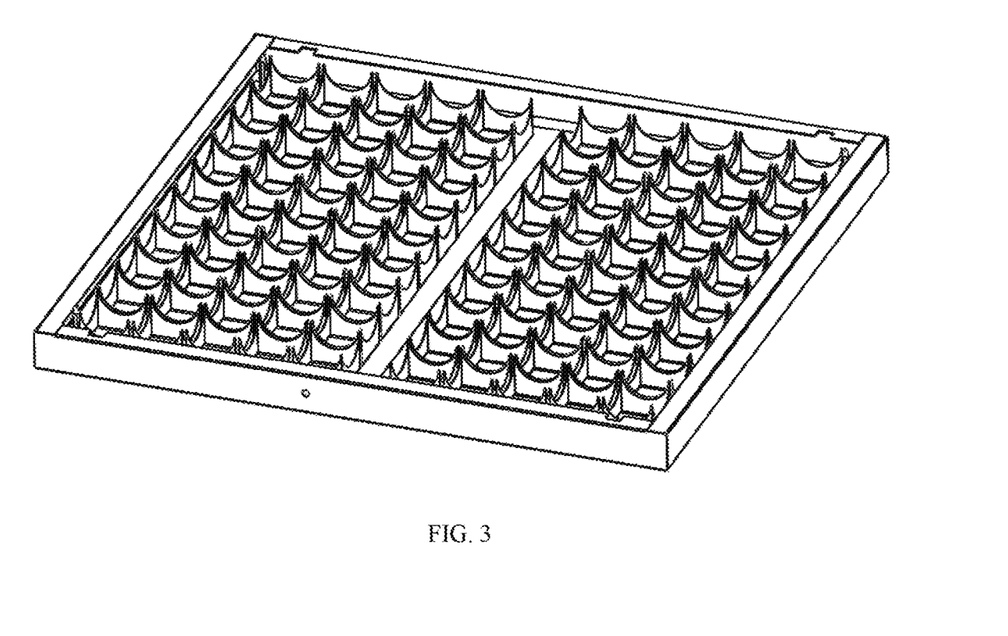
FIG. 3 is a stereoscopic view of a plasma generation device (a square barrel array) according to a preferred embodiment of the present disclosure.
Figure 4:
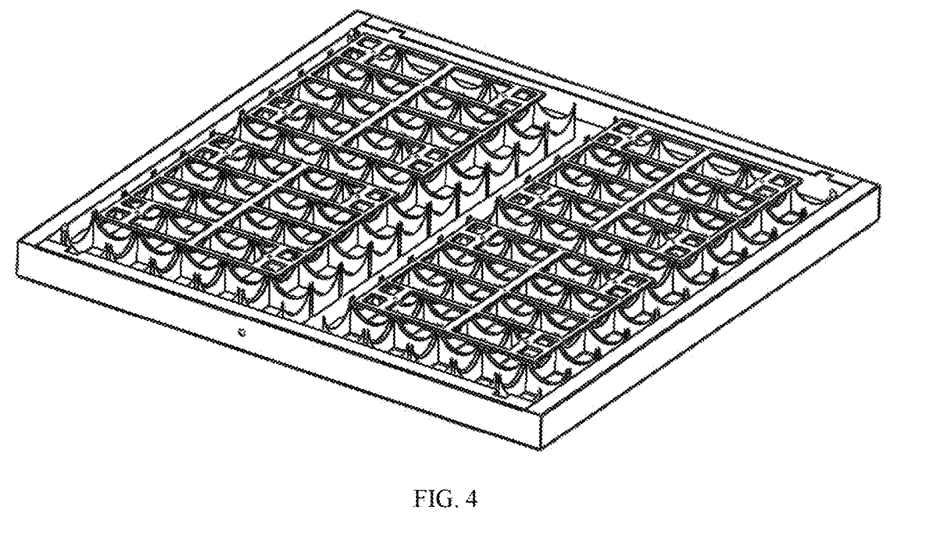
FIG. 4 is a stereoscopic view of a plasma generation device (with anode discharge) according to a preferred embodiment of the present disclosure.

However, only by simply changing the circular plasma generating barrel into the square plasma generating barrel, a new problem will arise. Distances from an endpoint of a discharge needle to four edges of the square plasma generating barrel are different. That is, there are far distances from the endpoint of the discharge needle to four corners of the square plasma generating barrel, and close distances from the endpoint of the discharge needle to midpoints of the four edges of the square plasma generating barrel. This lowers a plasma generation efficiency. In order to overcome the problem, an improvement is made to the edge of the square plasma generating barrel in the embodiment, as shown in FIG. 2. That is, a virtual sphere (with the endpoint of the discharge needle as a center) is used and is tangent to the edge of the square plasma generating barrel. A tangent line is taken as a new edge of the square plasma generating barrel. In this way, distances from the endpoint of the discharge needle to all points on the four edges of the square plasma generating barrel are identical, thereby solving the problem of the reduced plasma generation efficiency. As shown in FIG. 3 and FIG. 4, compared with the conventional circular generating barrel array, the plasma generation device provided by the embodiment increases an effective ventilation rate in a same frame area, or reduces the power and the size of the blower.

Embodiment 2

Figure 5:
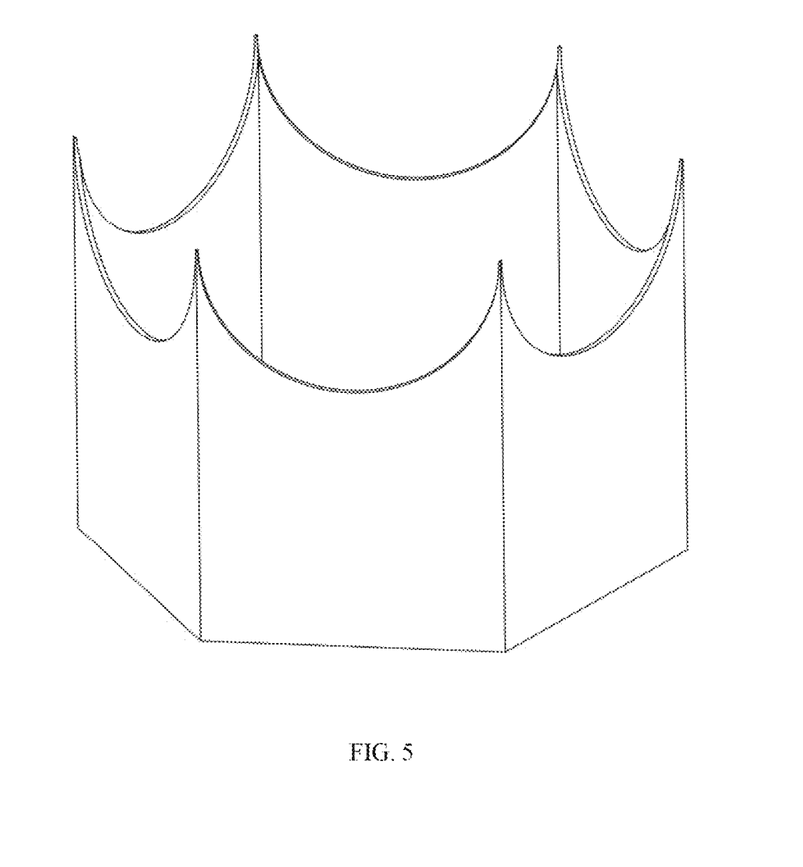
FIG. 5 is a schematic view of a single hexagonal plasma generating barrel according to a preferred embodiment of the present disclosure.
Figure 6:
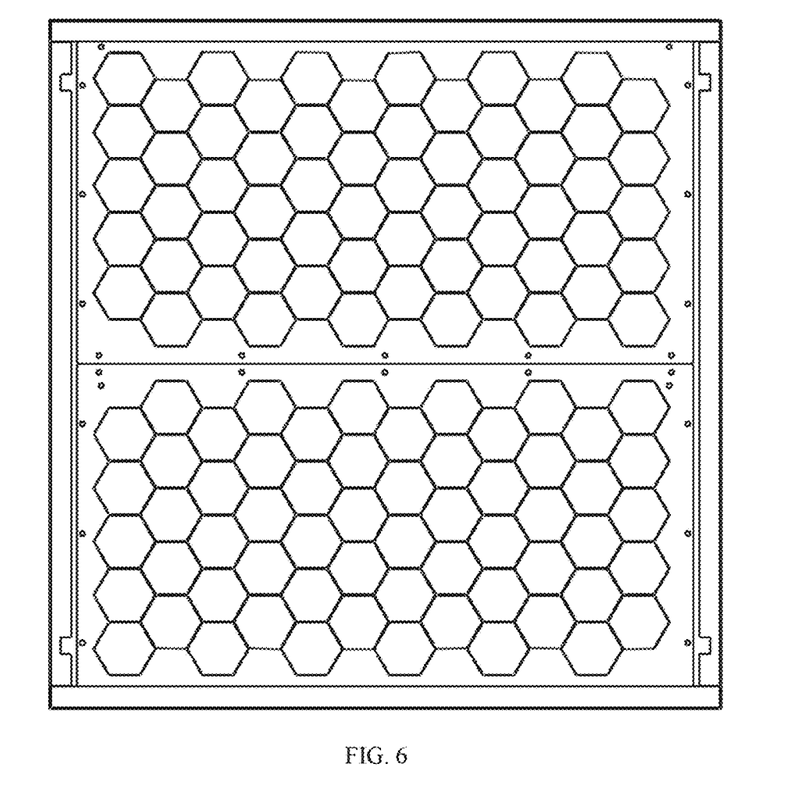
FIG. 6 is a plan view of a plasma generation device (a hexagonal array) according to a preferred embodiment of the present disclosure.
Figure 7:
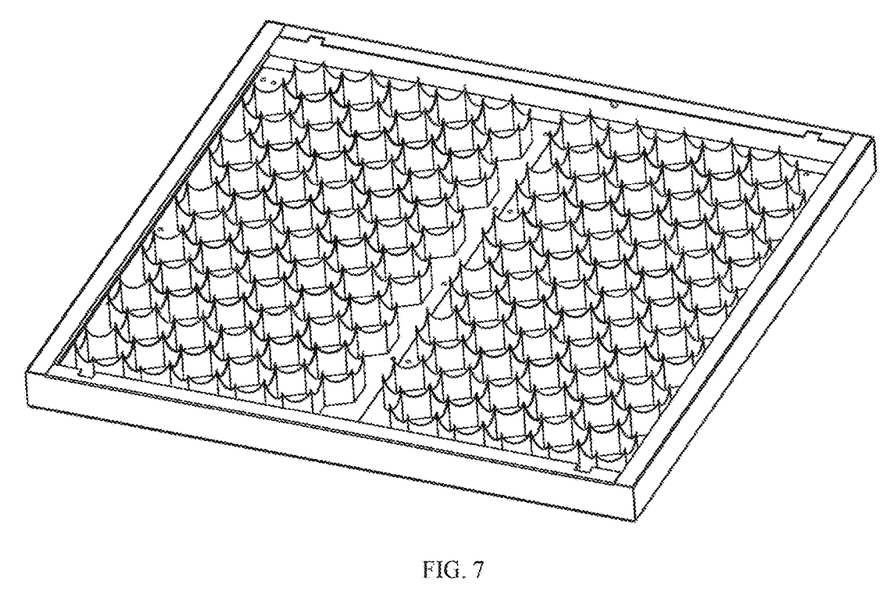
FIG. 7 is a stereoscopic view of a plasma generation device (a hexagonal array) according to a preferred embodiment of the present disclosure.

In the embodiment, as shown in FIG. 5, FIG. 6, and FIG. 7, the circular plasma generating barrel is changed into an orthohexagonal plasma generating barrel. Likewise, a top edge of the barrel is tangent to a virtual sphere with the endpoint of the discharge needle as a center. A resulting tangent line is taken as a new edge of the plasma generating barrel. In the embodiment, similar to the square plasma generating barrel, the orthohexagonal plasma generating barrel can also eliminate the inter-barrel gap, and maximize the effective ventilation rate in the same area.

Embodiment 3

Figure 8:
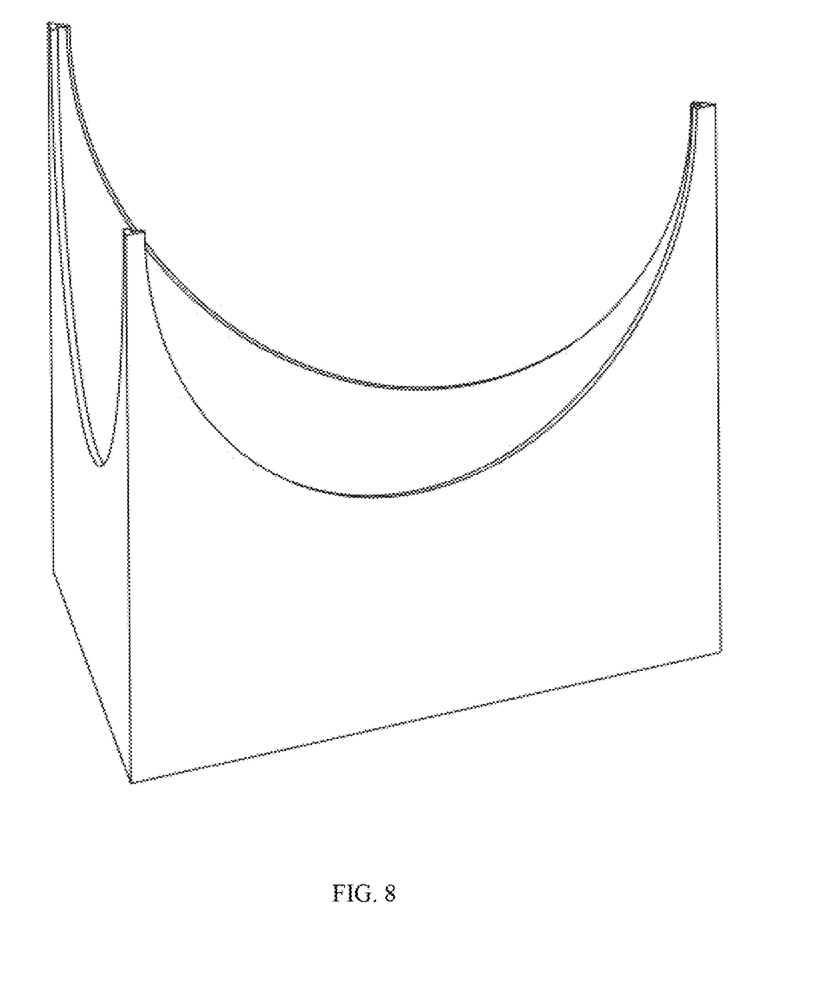
FIG. 8 is a schematic view of a single triangular plasma generating barrel according to a preferred embodiment of the present disclosure.
Figure 9:
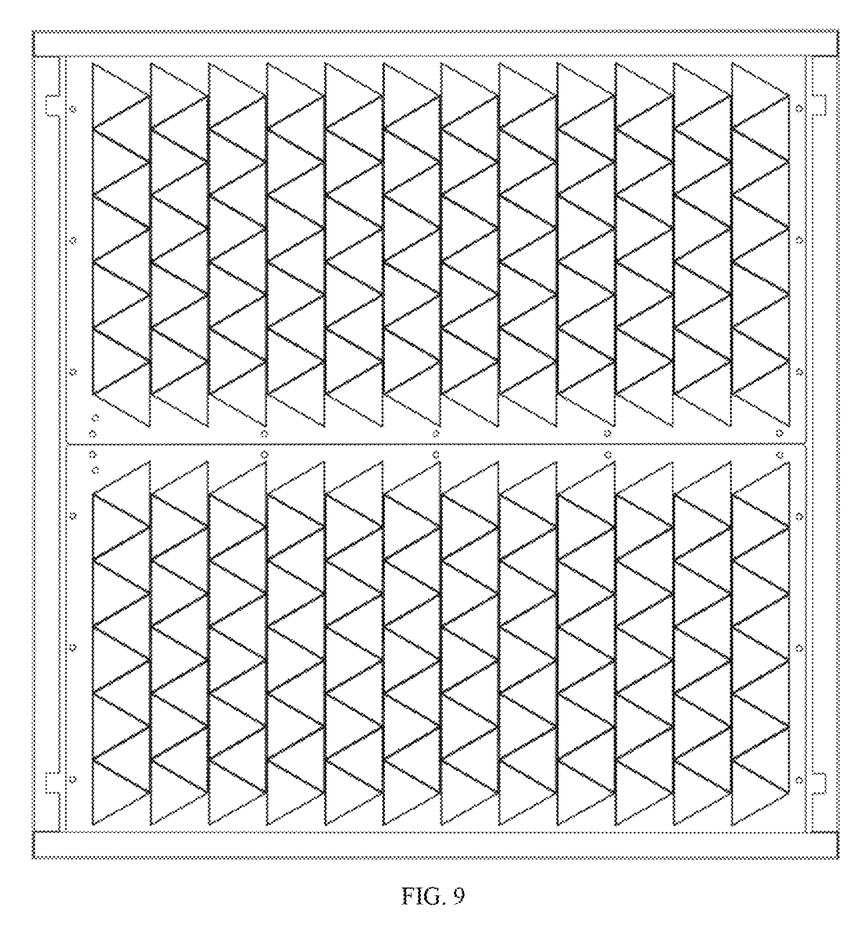
FIG. 9 is a plan view of a plasma generation device (a triangular array) according to a preferred embodiment of the present disclosure.
Figure 10:
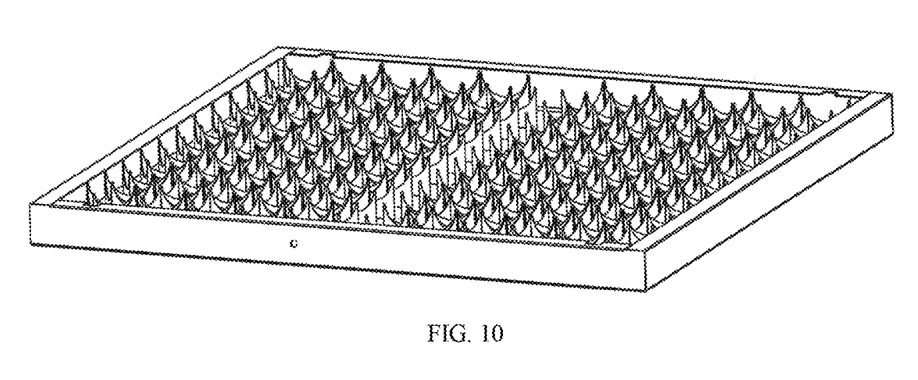
FIG. 10 is a stereoscopic view of a plasma generation device (a triangular array) according to a preferred embodiment of the present disclosure.

In the embodiment, as shown in FIG. 8, FIG. 9, and FIG. 10, the circular plasma generating barrel is changed into a regular triangular plasma generating barrel (an equilateral triangle). Likewise, a top edge of the barrel is tangent to a virtual sphere with the endpoint of the discharge needle as a center. A resulting tangent line is taken as a new edge of the plasma generating barrel. In the embodiment, similar to the square plasma generating barrel and the orthohexagonal plasma generating barrel, the regular triangular plasma generating barrel can also eliminate the inter-barrel gap, and maximize the effective ventilation rate under the same area.

Embodiment 4

Figures 13, 14:
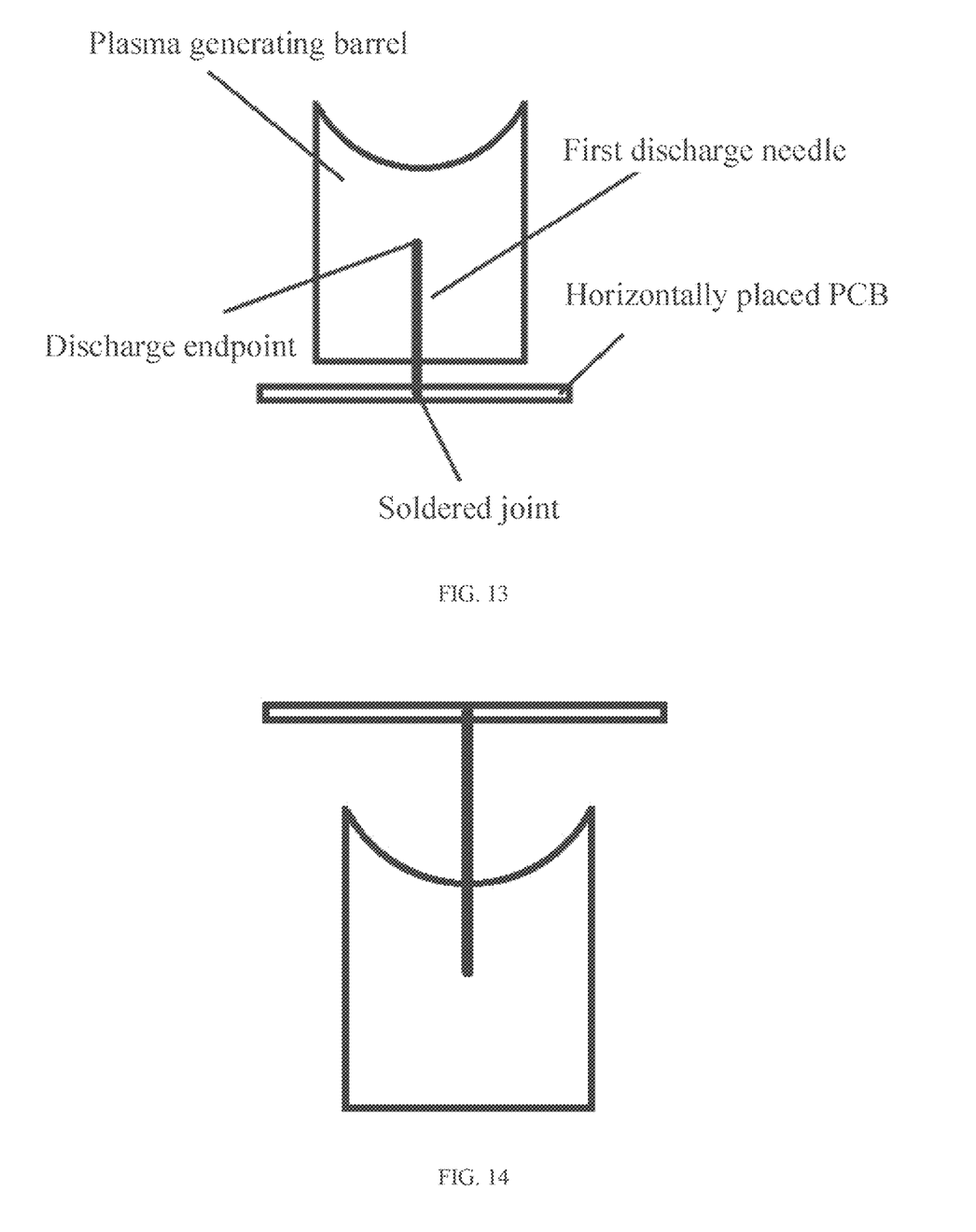
FIG. 13 is a schematic view of a plasma generation device (a lower horizontally-placed PCB) according to a preferred embodiment of the present disclosure.
FIG. 14 is a schematic view of a plasma generation device (an upper horizontally-placed PCB) according to a preferred embodiment of the present disclosure.

In Embodiment 1 to Embodiment 3, a PCB may be provided at a side of the plasma generating barrel away from the tangent sphere, as shown in FIG. 13. In this case, the discharge endpoint of the discharge needle cannot be higher than a lowest point of a circular arc of the new edge of the plasma generating barrel. The PCB may also be provided at a side of the plasma generating barrel tangent to the sphere, as shown in FIG. 14. In this case, the discharge endpoint of the discharge needle cannot be higher than a lowest point of the circular arc of the new edge of the plasma generating barrel.

Embodiment 5

Figure 15:
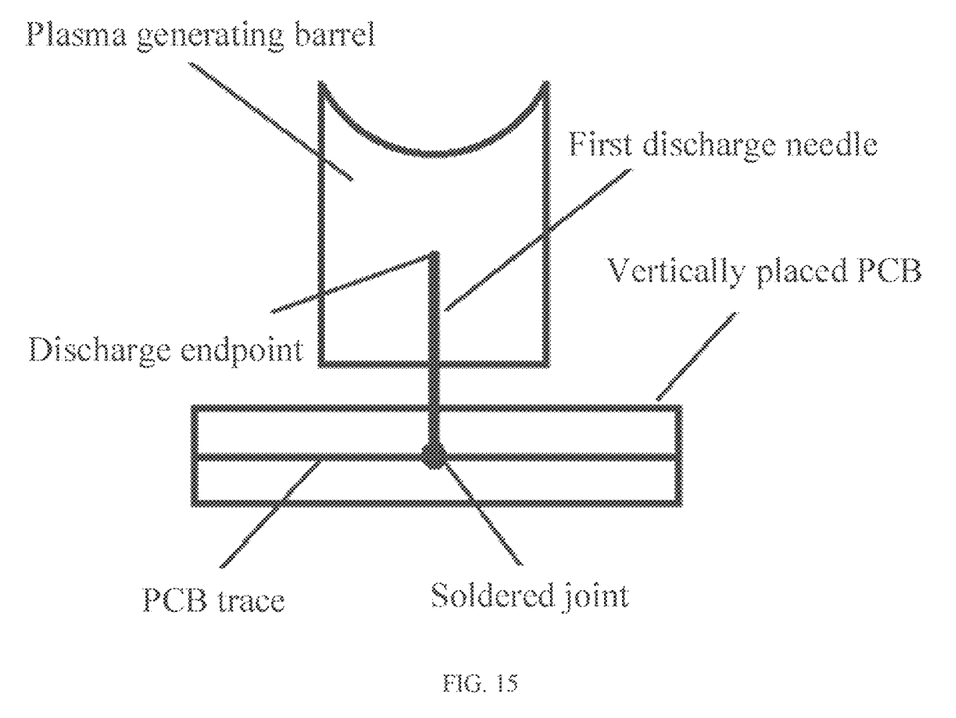
FIG. 15 is a schematic view of a plasma generation device (a lower vertically-placed PCB) according to a preferred embodiment of the present disclosure.
Figure 16:
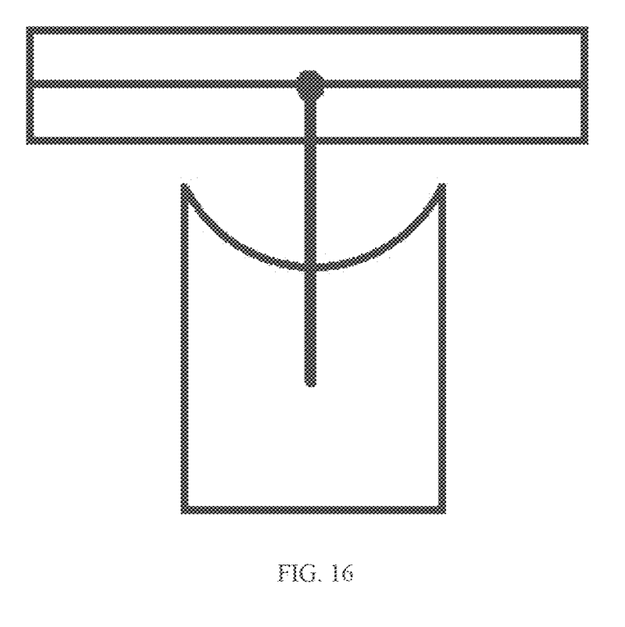
FIG. 16 is a schematic view of a plasma generation device (an upper vertically-placed PCB) according to a preferred embodiment of the present disclosure.

In the embodiment, as shown in FIG. 1 and FIG. 4, in order to keep a certain mechanical strength of the PCB, particularly in case of a large ventilation rate, the PCB must always have a certain width. In the embodiments, since an inter-barrel discharge needle (a second discharge needle) is to be added, the corresponding PCB is further provided synchronously. In this case, an area taken by the PCB is the same as or even greater than an area of the inter-barrel gap, as shown in FIG. 13 and FIG. 14. This will cause a problem with the loss outweighing the gain. In view of this problem, the PCB provided horizontally is provided vertically in the embodiment, as shown in FIG. 15 and FIG. 16. When the PCB is provided vertically (along a streamwise direction), a portion obstructing flowing of an airstream is merely the thickness of the PCB. This further maximizes the effective ventilation rate under the same area.

Embodiment 6

Figure 11:
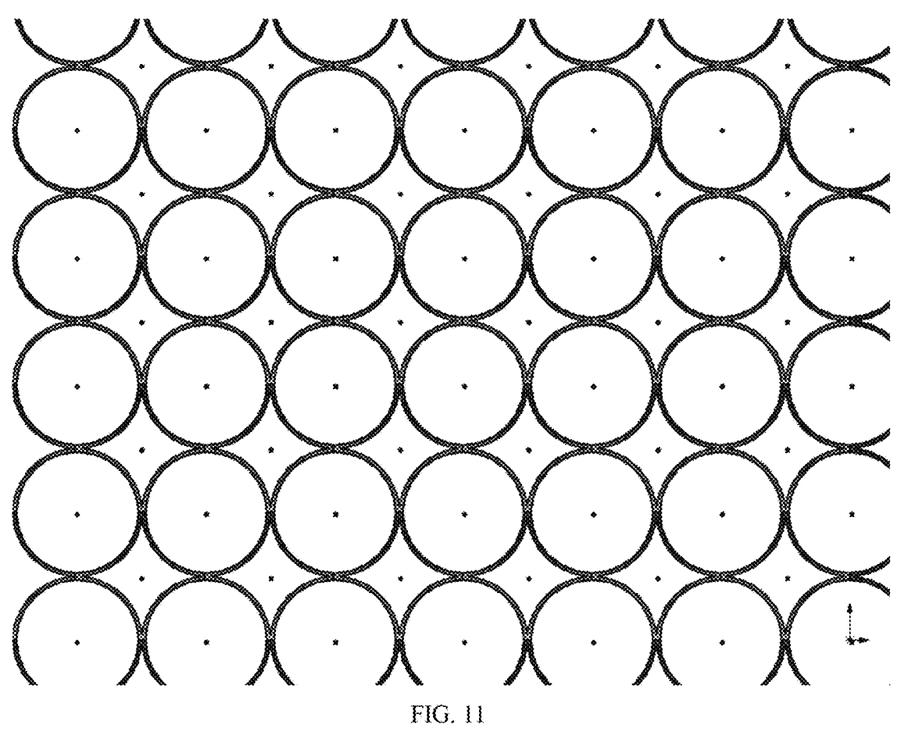
FIG. 11 is a plan view of a plasma generation device (a circular gap) according to a preferred embodiment of the present disclosure.
Figure 12:
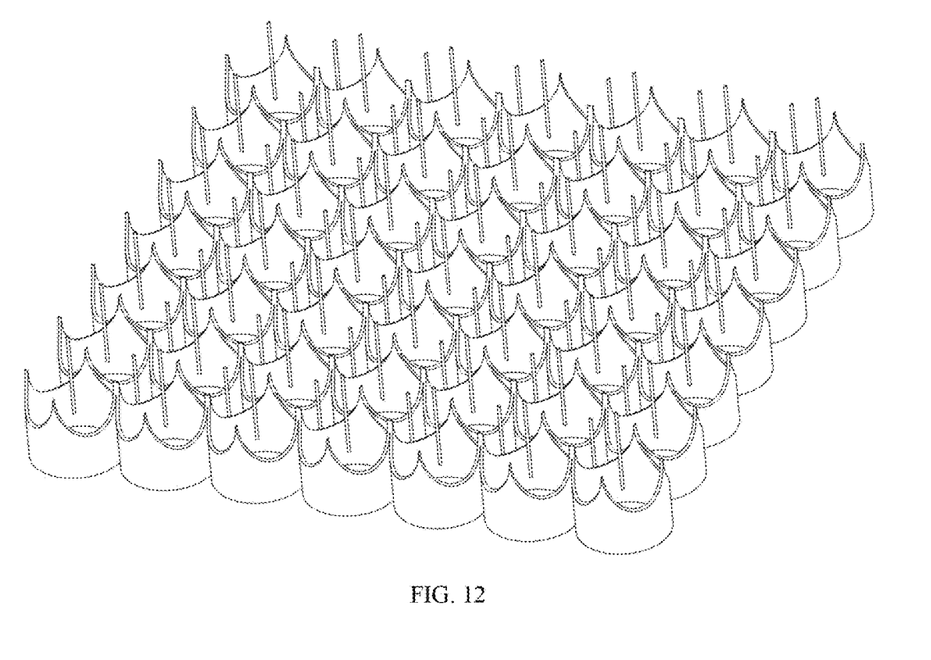
FIG. 12 is a stereoscopic view of a plasma generation device (a circular gap) according to a preferred embodiment of the present disclosure.
Figure 17:
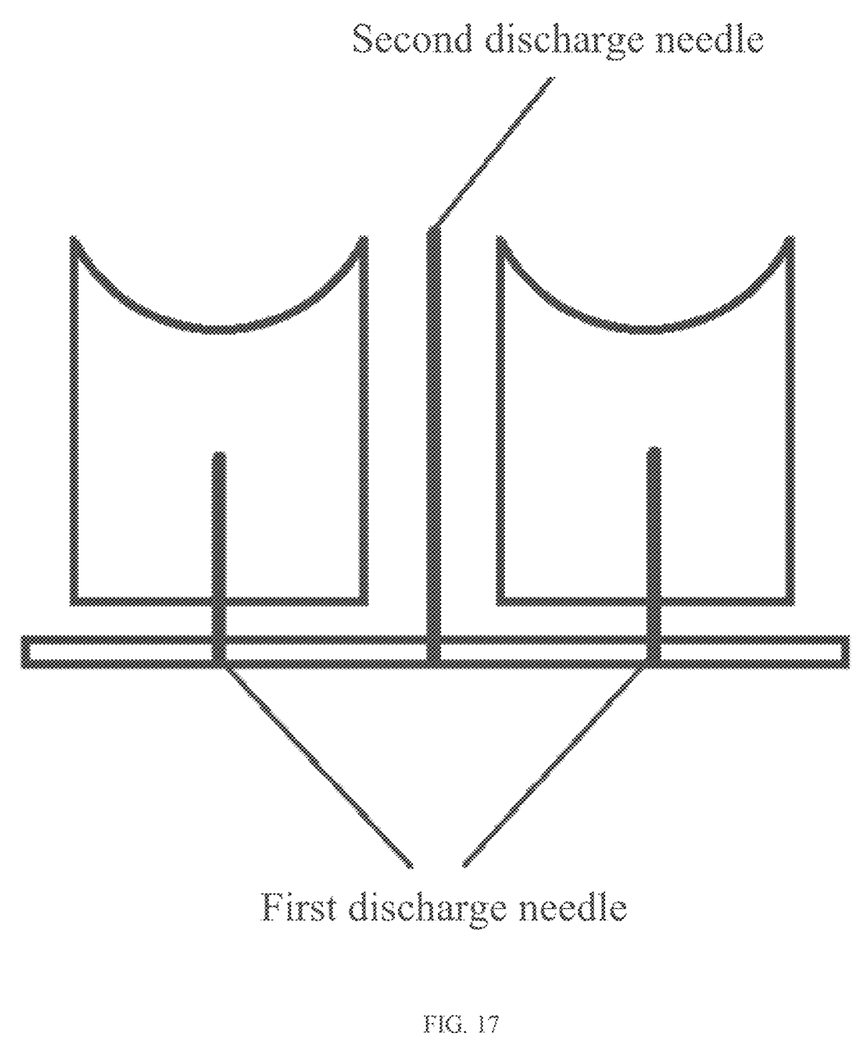
FIG. 17 is a schematic view of a plasma generation device (a second discharge needle and a lower PCB) according to a preferred embodiment of the present disclosure.
Figure 18:
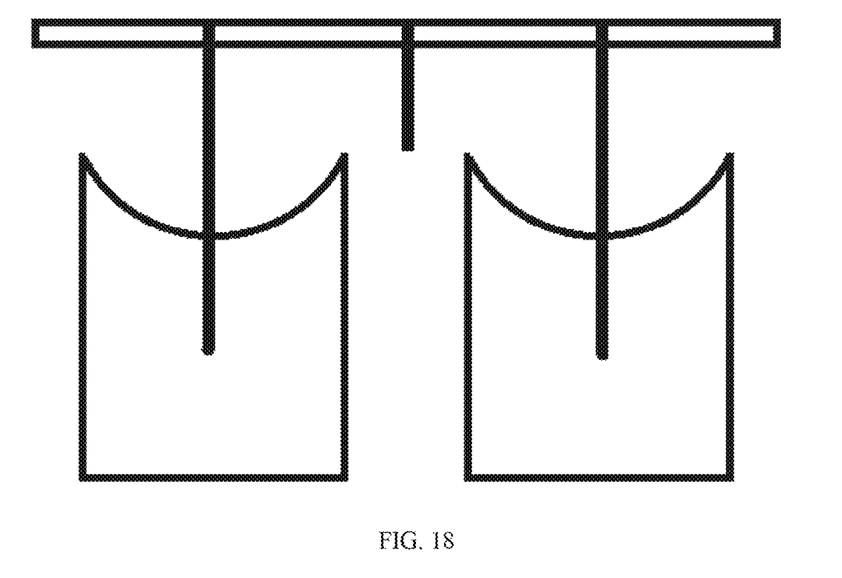
FIG. 18 is a schematic view of a plasma generation device (a second discharge needle and an upper PCB) according to a preferred embodiment of the present disclosure.

In another embodiment of the present disclosure, as shown in FIG. 11 and FIG. 12, the plasma generating barrel is still circular, but a clapboard in a gap among the circular barrels is removed. The PCB connected to an anode extends to a centerpoint of the inter-barrel gap. At the centerpoint, the second discharge needle is provided. With a discharge endpoint of the second discharge needle at the centerpoint of the inter-barrel gap as a center, a sphere is formed and is tangent to edges of barrels (four adjacent barrels enclosing the gap). A resulting tangent line is taken as a new edge of the plasma generating barrel. As shown in FIG. 17, in order to equidistantly keep a top end of the first discharge needle in the barrel to an upper edge of the tangent barrel, the discharge endpoint of the first discharge needle must be lower than a lowest point of a circular arc of the new upper edge of the barrel, and the discharge endpoint of the second discharge needle must be flush with a highest point of the circular arc of the new upper edge of the barrel. In addition, the PCB in the embodiment may also be provided at a side of the plasma generating barrel tangent to the sphere, as shown in FIG. 18.

Embodiment 7

Figure 19:
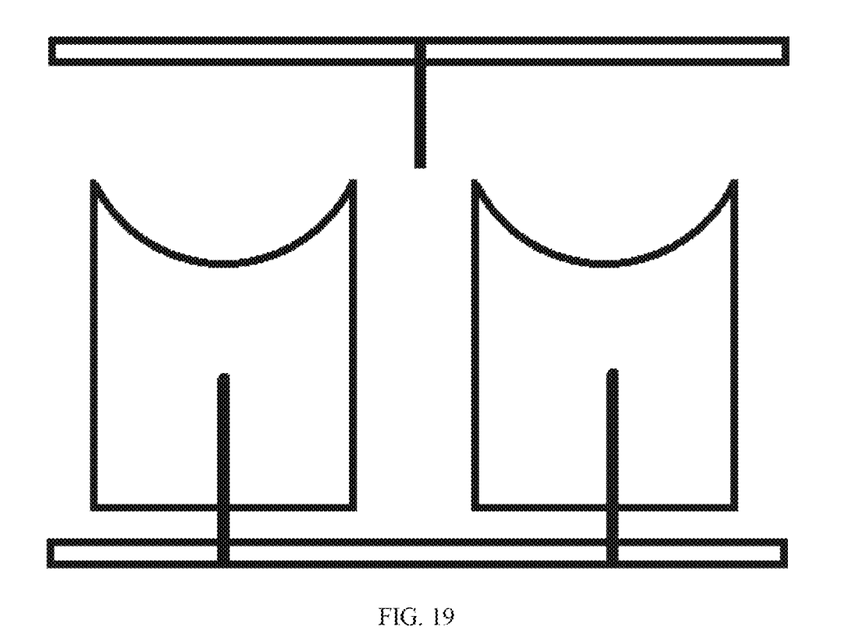
FIG. 19 is a schematic view of a plasma generation device (a second discharge needle and double PCBs) according to a preferred embodiment of the present disclosure.
Figure 20:
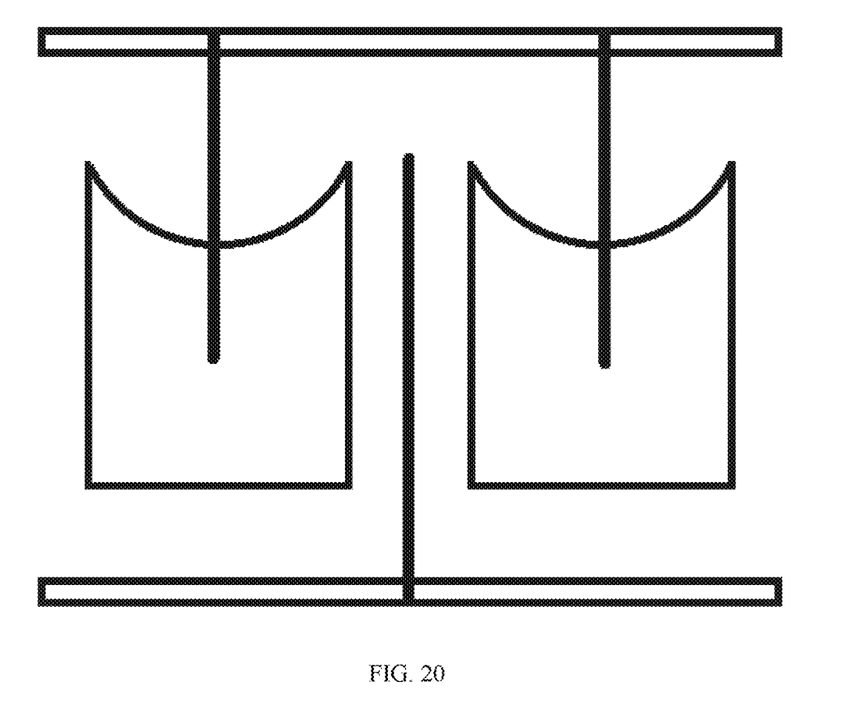
FIG. 20 is a schematic view of a plasma generation device (a second discharge needle and double PCBs) according to a preferred embodiment of the present disclosure.

On the basis of Embodiment 6, the first discharge needle and the second discharge needle are provided on different PCBs in the embodiment, as shown in FIG. 19 and FIG. 20.

Embodiment 8

Figure 21:
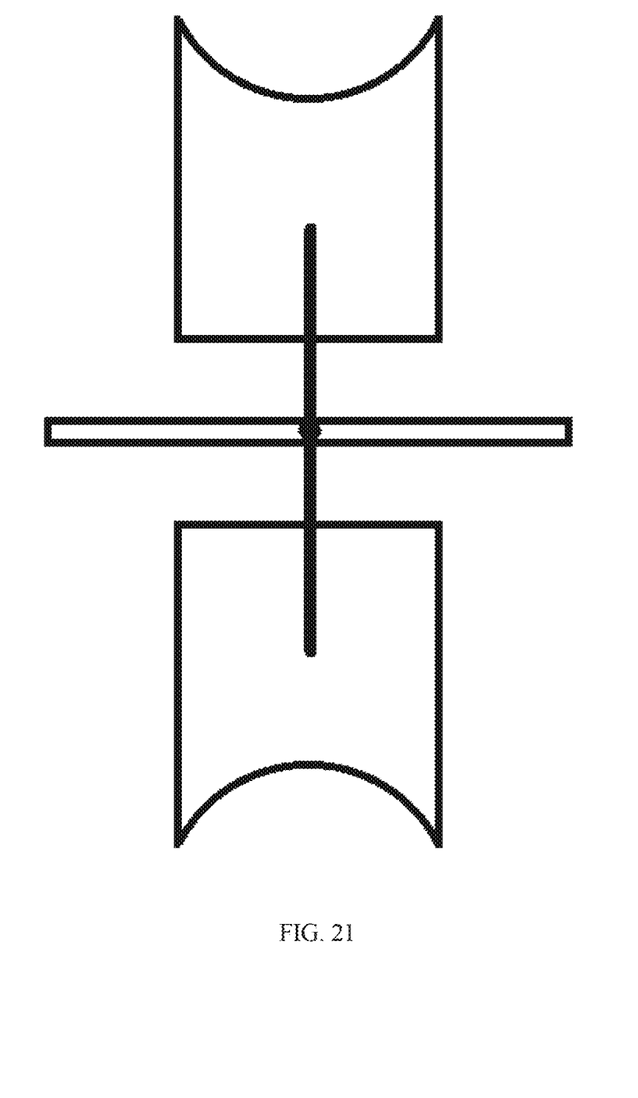
FIG. 21 is a schematic view of a plasma generation device (with a single needle, a single PCB, and double barrels) according to a preferred embodiment of the present disclosure.

In the embodiment, as shown in FIG. 21, two sides of the PCB are provided with the plasma generating barrels. Corresponding generating barrels at the two sides share one discharge needle.

In Embodiment 1 to Embodiment 8, the inventive concept of each embodiment can be combined with each other to form a new embodiment, and this is not repeated herein.

The foregoing is detailed description of the preferred specific embodiments of the present disclosure. It should be understood that a person of ordinary skill in the art can make various modifications and variations according to the concept of the present disclosure without creative efforts. Therefore, all technical solutions that a person skilled in the art can obtain based on the prior art through logical analysis, reasoning, or finite experiments according to the concept of the present disclosure shall fall within the protection scope defined by the appended claims.

What is claimed is:

1. A plasma generation device, comprising
    a frame,
    a first discharge needle, and
    plasma generating barrels, wherein
    the plasma generating barrels are square, orthohexagonal, or regular triangular; the plasma generating barrels form an array in the frame; the first discharge needle is provided on a geometric centerline in each of the plasma generating barrels; and a distance from a discharge endpoint of the first discharge needle to any point on an edge of the plasma generating barrel is identical.

2. The plasma generation device according to claim 1, wherein a virtual sphere is formed with the discharge endpoint of the first discharge needle as a center; the virtual sphere is tangent to the edge of the plasma generating barrel; and a resulting tangent line is taken as a new edge of the plasma generating barrel.

3. The plasma generation device according to claim 2, further comprising a PCB, wherein the first discharge needle is electrically connected to the PCB; and both the first discharge needle and the PCB are provided in a streamwise direction.

4. The plasma generation device according to claim 1, wherein the plasma generating barrels do not form an inter-barrel gap.

5. The plasma generation device according to claim 4, further comprising a PCB, wherein the first discharge needle is electrically connected to the PCB; and both the first discharge needle and the PCB are provided in a streamwise direction.

6. The plasma generation device according to claim 1, further comprising a PCB, wherein the first discharge needle is electrically connected to the PCB; and both the first discharge needle and the PCB are provided in a streamwise direction.

7. The plasma generation device according to claim 1, further comprising a PCB, wherein two sides of the PCB are provided with the plasma generating barrels; and corresponding plasma generating barrels at the two sides of the PCB share one discharge needle.

8. A plasma generation device, comprising
    a frame,
    a first discharge needle, and
    plasma generating barrels, wherein
    the plasma generating barrels form an array in the frame; the first discharge needle is provided on a geometric centerline in each of the plasma generating barrels; and a distance from a discharge endpoint of the first discharge needle to any point on an edge of the plasma generating barrel is identical; the plasma generating barrels are circular; and
    wherein a second discharge needle is provided at a geometric centerpoint in a gap of the array; a virtual sphere is formed with a discharge endpoint of the second discharge needle as a center; the virtual sphere is tangent to an edge of each of four adjacent plasma generating barrels; and a resulting tangent line is taken as a new edge of the plasma generating barrel.

9. The plasma generation device according to claim 8, wherein the discharge endpoint of the first discharge needle is not higher than a lowest point of the new edge of the plasma generating barrel; and the discharge endpoint of the second discharge needle is flush with a highest point of the new edge of the plasma generating barrel.

10. The plasma generation device according to claim 9, further comprising a PCB, wherein the first discharge needle is electrically connected to the PCB; and both the first discharge needle and the PCB are provided in a streamwise direction.

11. The plasma generation device according to claim 8, further comprising a printed circuit board (PCB), wherein the first discharge needle and the second discharge needle are provided on different PCBs.

12. The plasma generation device according to claim 11, further comprising the PCB, wherein the first discharge needle is electrically connected to the PCB; and both the first discharge needle and the PCB are provided in a streamwise direction.

13. The plasma generation device according to claim 8, further comprising a PCB, wherein the first discharge needle is electrically connected to the PCB; and both the first discharge needle and the PCB are provided in a streamwise direction.

* * * * *